United States Patent [19]

Isoda et al.

[11] Patent Number: 4,898,943

[45] Date of Patent: Feb. 6, 1990

[54] TRICYCLIC TRIAZOLOPYRIMIDINE DERIVATIVES

[75] Inventors: Sumiro Isoda; Shunzo Aibara; Tamotsu Miwa; Hiroyuki Fujiwara; Shuichi Yokohama; Hiroo Matsumoto, all of Tokyo, Japan

[73] Assignee: Daiichi Seiyaku Co., Ltd., Tokyo, Japan

[21] Appl. No.: 153,677

[22] Filed: Feb. 8, 1988

[30] Foreign Application Priority Data

Feb. 6, 1987 [JP] Japan ................................. 62-25853
Mar. 30, 1987 [JP] Japan ................................. 62-77344

[51] Int. Cl.$^4$ .................... C07D 513/14; A61K 31/52
[52] U.S. Cl. .................................. 544/251; 544/255; 544/278; 548/138; 548/199
[58] Field of Search ........................................ 544/251

[56] References Cited

U.S. PATENT DOCUMENTS 4,223,031  9/1980  Covington et al. ............. 544/250 X
4,366,156 12/1982  Temple, Jr. ....................... 514/267
4,652,646  3/1987  Isoda et al. ......................... 544/251

FOREIGN PATENT DOCUMENTS 0159707 10/1985  European Pat. Off. .

OTHER PUBLICATIONS

European Search Report.

*Primary Examiner*—Mukund J. Shah
*Assistant Examiner*—Diana G. Rivers
*Attorney, Agent, or Firm*—Sughrue, Mion, Zinn, Macpeak & Seas

[57] ABSTRACT

Novel tricyclic triazolopyrimidine compounds represented by formula (I) shown in the specification and physiologically acceptable salts thereof are disclosed. These compounds have an excellent anti-allergic activity and are useful for treatment and prophylaxis of allergic diseases.

15 Claims, No Drawings

TRICYCLIC TRIAZOLOPYRIMIDINE DERIVATIVES

FIELD OF THE INVENTION

Leukotriene D4 (hereinafter abbreviated as LTD$_4$) has recently become important as one of chemical mediators which are released by various stimulations, such as immune reactions, and induce allergy. Accordingly, an importance of antagonistic activity against LTD$_4$ has been increasing as an index of anti-allergic activity.

Structurally relevant to the compounds according to the present invention are those disclosed in U.S. Pat. No. 4,652,646. The publication reports that those compounds possess an inhibitory activity on release of histamine and a so-called "slow reacting substance of anaphylaxis" and an inhibitory activity on passively sensitized rat cutaneous anaphylaxis (hereinafter referred to as PCA), however, does not disclose an LTD$_4$ antagonistic activity.

SUMMARY OF THE INVENTION

An object of this invention is to provide a compound having an excellent LTD$_4$ antagonistic activity.

As a result of extensive investigations, the present inventors have found that the tricyclic triazolopyrimidine derivatives represented by formula (I) shown below exhibit an excellent LTD$_4$ antagonistic activity and reached the present invention.

The present invention relates to a compound represented by formula (I)

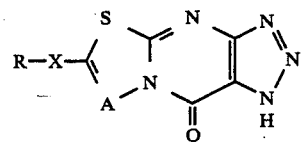

wherein A represents

or =N—; A' represents a hydrogen atom, an alkyl group or a halogen-substituted alkyl group; R represents an alkyl group, a halogen-substituted alkyl group, an alkenyl group, a halogen-substituted alkenyl group, or a cycloalkyl group or a cycloalkenyl group, each of which may be substituted with one or more substituents selected from the group consisting of a hydroxyl group, an alkyl group, an alkoxy group, a halogen atom, an amino group, and a halogen-substituted alkyl group; and X represents a single bond, or an alkylene group or an alkenylene group, each of which may be substituted with one or more substituents selected from the group consisting of an alkoxy group and a halogen atom, and a physiologically acceptable salt thereof.

DETAILED DESCRIPTION OF THE INVENTION

In formula (I), the alkyl group has 1 to 6 carbon atoms, and includes methyl, ethyl, propyl, isopropyl, butyl, t-butyl groups, etc. The alkoxy group has 1 to 6 carbon atoms, and includes methoxy, ethoxy, propoxy, butoxy groups, etc. The halogen atom includes fluorine, chlorine, bromine, and iodine atoms. The halogen-substituted alkyl group has 1 to 6 carbon atoms, and means alkyl groups substituted with one or more of the above-described halogen atoms, e.g., a halogenomethyl, halogenoethyl, halogenobutyl, dihalogenomethyl, dihalogenobutyl or trihalogenomethyl group. The alkenyl group has 1 to 6 carbon atoms, and includes vinyl, propenyl, butenyl groups, etc. The halogen-substituted alkenyl group has 1 to 6 carbon atoms, and means the above-described alkenyl group substituted with one or more of the above-described halogen atoms, e.g., halogenopropenyl, halogenobutenyl groups, etc. The cycloalkyl group has 4 to 14 carbon atoms, preferably 5 to 12 carbon atoms, and includes cyclobutyl, cyclopentyl, cyclohexyl, cycloheptyl, cyclooctyl, cyclononyl, cyclodecyl, cycloundecyl, cyclododecyl groups, etc. The cycloalkenyl group has 5 to 14 carbon atoms, preferably 5 to 10 carbon atoms, and includes cycloheptenyl, cyclohexenyl, cyclooctenyl, cyclodecenyl, cyclododecenyl groups, etc. The alkylene group has 1 to 10 carbon atoms, preferably 1 to 4 carbon atoms, and means a methylene, polymethylene group, or a methylene or polymethylene group which is substituted with one or more alkyl groups. Examples thereof include methylene, ethylene, trimethylene, propylene, ethylethylene, tetramethylene groups, etc. The alkenylene group has 2 to 10 carbon atoms, preferably 2 to 4 carbon atoms, and means the group formed by eliminating two hydrogen atoms from the same or different carbon atom(s) of an alkene. Examples thereof include vinylene, propenylene, 1-butenylene, 2-butenylene, 2-pentenylene, 2-methyl-1-butenylene, 2-methyl-2-butenylene, 4-propyl-2-pentenylene groups, etc.

The salts of the compounds of formula (I) include salts with an alkali metal, e.g., sodium, potassium, etc., an alkaline earth metal, e.g., calcium, magnesium, etc., ammonia, an amine, e.g., tris(hydroxymethyl)aminomethane, N-methylglucamine, or a basic amino acid, e.g., lysine, arginine, etc.

For the sake of convenience, the compounds of the present invention are represented in the form of 1H-9-oxo compounds. However, the compounds of the present invention have tautomers represented by formulae (I'), (I''), and (I''') below. And it should be noted that these tautomers as well as mixture thereof are also included in the scope of the present invention.

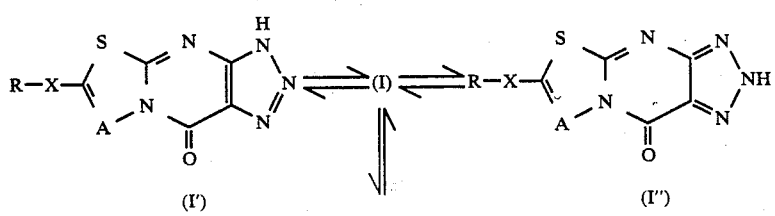

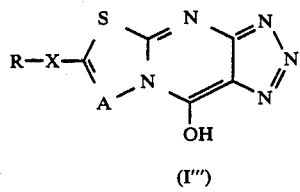

(I''')

Further, some of the compounds of formula (I) have various optical or stereo isomers attributed to their partial structures, R and X, and these isomers as well as mixtures thereof are also included in the scope of the present invention.

Of the compounds represented by formula (I) according to the present invention, preferred are those wherein X is an alkylene group or an alkenylene group and R is a cycloalkyl group which may be substituted with one or more alkyl groups. More preferred are those wherein X is an ethylene group, a propylene group or a vinylene group; R is a cycloalkyl group having from 5 to 7 carbon atoms which may be substituted with an alkyl group; and A is CH or N.

The compounds of formula (I) can be prepared by diazotizing a compound represented by formula (II)

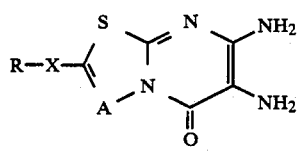

wherein A, R and X are as defined above.

In carrying out the above diazotization reaction, the compound represented by formula (II) or a salt thereof is added to an adequate amount of an acidic solvent to prepare an acidic solution or suspension and then reacted with a nitrite. The reaction is usually carried out under ice-cooling or at a temperature up to room temperature (about 2° to 30° C.) for a period of from 30 minutes to one day. The acidic solvent to be used includes inorganic acids, e.g., hydrochloric acid, hydrobromic acid, etc., organic acids, e.g., acetic acid, propionic acid, etc., and mixtures thereof. The nitrite to be used includes sodium nitrite, potassium nitrite, and the like. The nitrite is usually used in at least an equimolar amount to the compound of formula (II).

Alternatively, the above diazotization can be carried out by treating the compound of formula (II) or a salt thereof under other diazotizing conditions, for example, by treating the compound of formula (II) with a nitrous acid ester, e.g., isoamyl nitrite, etc., in an adequate amount of the above-described acidic solvent. In this reaction, the nitrous acid ester is usually used in at least an equimolar amount to the compound of formula (II).

The starting compounds of formula (II) are novel compounds and can be prepared through the following reaction scheme:

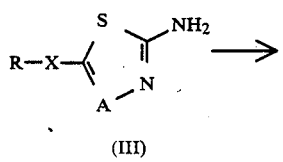

(III)

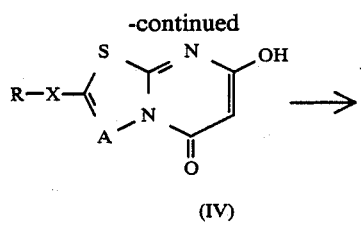

(IV)

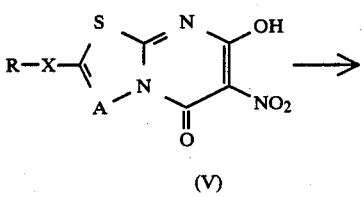

(V)

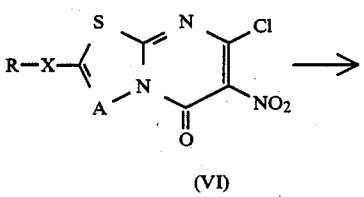

(VI)

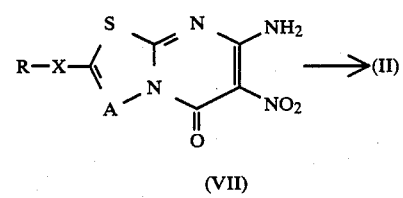

(VII)

wherein A, R and X are as defined above.

The process for preparing the starting compound of formula (II) are hereinafter described in detail.

The compound of formula (III) is reacted with a malonic ester, preferably, 2,4,6-trichlorophenyl malonate, in the presence or absence of an inert solvent, such as xylene, Dowtherm A, etc., to obtain the compound of formula (IV). The reaction is generally carried out at a temperature of from 100° C. to 250° C. for a period of from 0.5 to 10 hours.

The compound of formula (IV) is reacted with fuming nitric acid in the presence or absence of an inert solvent, such as acetic acid, diethyl ether, etc., to prepare the compound of formula (V). The reaction is usually carried out at a temperature of from −10° C. to 80° C. for a period of from 0.5 to 15 hours.

The compound of formula (V) is reacted with phosphorous oxychloride in the presence of an acid acceptor with or without an inert solvent to prepare the compound of formula (VI). The acid acceptor preferably includes organic bases, e.g., dimethylaniline, diethylaniline, tripropylamine, etc. The reaction is usually carried out at a temperature of from room temperature to 100° C. for a period of from 0.5 to 5 hours.

The compound of formula (VI) is reacted with ammonia in the presence or absence of an inert solvent, e.g., alcohols, dioxane, etc., to prepare the compound of formula (VII). The reaction is usually carried out under ice-cooling or at a temperature up to 80° C. for a period of from 0.5 to 5 hours.

The compound of formula (VII) is then subjected to reduction in a conventional manner, such as catalytic reduction or reduction using a metal and an acid to thereby obtain the compound of formula (II).

The starting compound of formula (III) can be prepared by the following processes:

Process A:

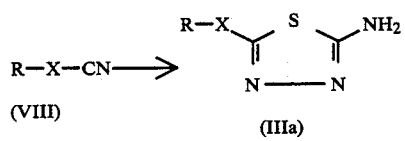

wherein R and X are as defined above.

The compound of formula (IIIa) can be prepared by reacting the compound of formula (VIII) with thiosemicarbazide in trifluoroacetic acid at a temperature near to the boiling point of trifluoroacetic acid and then reacted with ammonia at a temperature of from room temperature to about 80° C.

Process B:

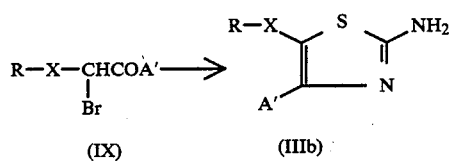

wherein R, X and A' are as defined above.

The compound of formula (IIIb) can be prepared by reacting the compound of formula (IX) with thiourea in an alcohol solvent, e.g., ethanol, etc., at about 80° C.

Process C:

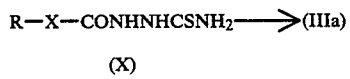

wherein R and X are as defined above.

The compound of formula (IIIa) can also be prepared by reacting the compound of formula (X) with a dehydrating agent, e.g., sulfuric acid, phosphorous tribromide, phosphorous oxychloride, etc., in the absence of a solvent at a temperature of from room temperature to about 150° C.

Process D:

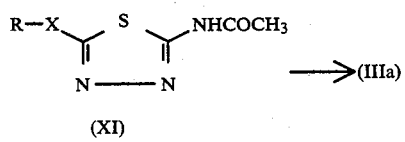

wherein R and X are as defined above.

The compound of formula (IIIa) can also be prepared by hydrolyzing the compound of formula (XI) with an alkali or an acid in a hydrous alcohol.

Process E:

wherein R, X and A' are as defined above.

The compound of formula (IIIb) can also be prepared by reacting the compound of formula (XII) with thiourea in the presence of iodine with or without a solvent at a temperature of from about 100° C. to 120° C.

The starting compounds of formulae (VIII) to (XII) can be obtained by appropriately combining known processes.

The compounds according to the present invention exhibit an excellent $LTD_4$ antagonistic activity and significantly inhibit PCA by oral administration. Therefore, the compounds of the present invention are useful for treatment and prophylaxis of allergic diseases, such as bronchial asthma, allergic gastro-intestinal disorders, allergic conjunctivitis, allergic rhinitis, hay fever, urticaria, inflammatory diseases, and the like.

The compounds of the present invention can be administered orally or parenterally.

For the oral administration, the compounds of the present invention may be used at a dosage of 10 mg to 300 mg in adult human per day in the form of various pharmaceutical preparations such as tablets, capsules, powders, granules, syrups and the like. The preparations can be prepared by the conventional techniques known in the art.

Examples of the preparation containing the compound of the present invention are described below.

| Tablets | |
|---|---|
| Compound of the present invention | 50 mg |
| Lactose | 35 mg |
| Hydroxypropyl Cellulose | 3 mg |
| Starch | 21.5 mg |
| Magnesium Stearate | 0.5 mg |
| | 110 mg/one tablet |
| Syrups | |
| Compound of the present invention | 1,000 mg |
| Polysorbate 80 | 100 mg |
| Simple syrup | adequate amount |
| | 100 ml |

The present invention is now illustrated in greater detail by the following Examples, Reference Examples, and Test Examples, but it should be understood that the present invention is not limited thereto.

EXAMPLE 1

6-(2-Cyclohexylethyl)-[1,3,4]thiadiazolo-[3,2-a][1,2,3]triazolo[4,5-d]pyrimidin-9-(1H)-one In 100 ml of dioxane were suspended 6.46 g of 7-amino-2-(2-cyclohexylethyl)-6-nitro-5H-[1,3,4]thiadiazolo[3,2-a]pyrimidin-5-one and 11.9 g of tin powder, and 14.4 ml of concentrated hydrochloric acid was added thereto dropwise while gently refluxing. After being refluxed for 1 hour, any insoluble matters were removed by filtration. The filtrate was concentrated under reduced pressure, and isopropanol was added thereto. The formed precipitate was collected by filtration, suspended in a mixture of 200 ml of concentrated hydrochloric acid and 200 ml of water, and cooled to −5° to 0° C. While stirring, 40 ml of an aqueous solution of 5.0 g of sodium nitrite was then added dropwise to the suspension. The stirring was continued for an additional 5.5 hours under ice-cooling, and the resulting precipitate was collected by filtration and recrystallized from 95% ethanol to obtain 2.0 g of the titled compound as a pale yellow crystal. Melting point: 265°–270° C. (decomposition).

EXAMPLES 2 TO 19

In the same manner as described in Example 1, each of the following compounds represented by formula (I) was prepared.

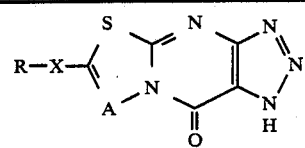

| Example No. | A | R—X— | Melting Point (°C.) |
|---|---|---|---|
| 2 | N | cyclopentyl-(CH$_2$)$_2$— | 271–275 (decomp.) |
| 3 | N | cyclopentyl-(CH$_2$)$_3$— | 269–271 |
| 4 | N | cyclohexyl-CH$_2$— | 285–290 (decomp.) |
| 5 | N | cyclohexyl-(CH$_2$)$_3$— | 268–271 |
| 6 | N | CH$_3$-cyclohexyl-(CH$_2$)$_2$— | 282–285 |
| 7 | N | CH$_3$-cyclohexyl-(CH$_2$)$_2$— | 270–272 |
| 8 | N | CH$_3$-cyclohexyl-(CH$_2$)$_2$— | 274–276 |
| 9 | N | cyclopentyl-(CH$_2$)$_2$— | 257–270 (decomp.) |
| 10 | CH | cyclopentyl-(CH$_2$)$_2$— | 201–203 |
| 11 | CH | cyclohexyl-(CH$_2$)$_2$— | 202–204 |
| 12 | N | CH$_3$(CH$_2$)$_7$— | 231–232 |
| 13 | N | (CH$_3$)$_3$C(CH$_2$)$_2$— | 275–279 (decomp.) |
| 14 | N | (CH$_3$CH$_2$)$_2$CH(CH$_2$)$_2$— | 255–260 |
| 15 | N | bicyclic-(CH$_2$)$_2$— | 282–290 (decomp.) |
| 16 | C—CH$_3$ | cyclohexyl-(CH$_2$)$_2$— | 175–178 |
| 17 | N | cyclohexyl-CH=CH— (E form) | 256–260 |
| 18 | N | CH$_3$-cyclohexyl-(CH$_2$)$_2$— | 251–254 |
| 19 | N | diamond-(CH$_2$)$_2$— | 269–273 |

Elemental analysis, nuclear magnetic resonance spectrum, and infrared absorption spectrum of the compounds of Examples 1 to 19 are shown below.

| Example No. | Formula | Elemental Analysis % (calcd.)/(found) | | | NMR Spectrum (solvent) δ | IR Spectrum (KBr) cm$^{-1}$ |
|---|---|---|---|---|---|---|
| | | C | H | N | | |
| 1 | C$_{13}$H$_{16}$N$_6$OS | 51.30 | 5.30 | 27.61 | (CDCl$_3$—TFA) | 2926, 2848, 1713, 1578, |
| | | 51.01 | 5.41 | 27.54 | 0.80–1.90 (m, 13H) | 1536 |
| | | | | | 3.10 (t, 2H) | |
| 2 | C$_{12}$H$_{14}$N$_6$OS | 49.64 | 4.86 | 28.95 | (CDCl$_3$—TFA) | 1707, 1572, 1530 |
| | | 49.74 | 4.90 | 29.31 | 1.00–2.00 (m, 11H) | |
| | | | | | 3.14 (t, 2H) | |
| 3 | C$_{13}$H$_{16}$N$_6$OS | 51.30 | 5.30 | 27.61 | (CDCl$_3$—TFA) | 2944, 2860, 1710, 1572, |

-continued

| Example No. | Formula | Elemental Analysis % (calcd.)/(found) | | | NMR Spectrum (solvent) δ | IR Spectrum (KBr) cm$^{-1}$ |
|---|---|---|---|---|---|---|
| | | C | H | N | | |
| | | 51.53 | 5.26 | 27.77 | 0.80–2.00 (m, 13H) 3.09 (t, 2H) | 1533 |
| 4 | $C_{12}H_{14}N_6OS$ | 49.64 49.40 | 4.86 4.92 | 28.95 28.72 | (DMSO—$d_6$) 0.80–2.00 (m, 11H) 2.94 (d, 2H) | 3184, 2920, 1713, 1572, 1530 |
| 5 | $C_{14}H_{18}N_6OS$ | 52.81 52.76 | 5.70 5.77 | 26.40 26.30 | (DMSO—$d_6$) 0.60–2.00 (m, 15H) 3.02 (t, 2H) | 3178, 2920, 2848, 1713, 1572, 1533 |
| 6 | $C_{14}H_{18}N_6OS$ | 52.81 52.86 | 5.70 5.69 | 26.40 26.58 | (CDCl$_3$—TFA) 0.87 (d, 3H) 0.80–1.95 (m, 12H) 3.08 (t, 2H) | 2920, 2854, 1713, 1575, 1536 |
| 7 | $C_{14}H_{18}N_6OS$ | 52.81 52.87 | 5.70 5.68 | 26.40 26.58 | (CDCl$_3$—TFA) 0.90 (d, 3H) 0.60–1.95 (m, 12H) 3.12 (t, 2H) | 2920, 2848, 1713, 1578, 1536 |
| 8 | $C_{14}H_{18}N_6OS \cdot H_2O$ | 49.47 49.44 | 5.99 5.50 | 24.98 25.05 | (CDCl$_3$—TFA) 0.88 (d, 3H) 0.80–1.90 (m, 12H) 3.20 (t, 2H) | 2920, 2848, 1716, 1575, 1536 |
| 9 | $C_{14}H_{18}N_6OS$ | 52.81 52.98 | 5.70 5.82 | 26.40 26.48 | (DMSO—$d_6$) 1.00–1.90 (m, 15H) 3.05 (t, 2H) | 2920, 1704, 1575, 1527 |
| 10 | $C_{13}H_{15}N_5OS$ | 53.96 53.98 | 5.23 5.34 | 24.20 24.04 | (CDCl$_3$—TFA) 0.8–1.9 (m, 11H) 2.8–3.0 (m, 2H) 7.92 (s, 1H) | 3120, 2944, 1734, 1581, 1570, 1455 |
| 11 | $C_{14}H_{17}N_5OS$ | 55.43 55.65 | 5.65 5.82 | 23.08 22.98 | (CDCl$_3$—TFA) 0.8–1.9 (m, 13H) 2.79–2.96 (m, 2H) 7.92 (s, 1H) | 3172, 3124, 2926, 2848, 1695, 1578, 1530, 1470 |
| 12 | $C_{13}H_{18}N_6OS$ | 50.96 50.78 | 5.92 5.96 | 27.43 27.32 | (DMSO—$d_6$) 0.70–2.0 (m, 15H) 3.04 (m, 2H) | 3180, 2928, 2852, 1714, 1576, 1536 |
| 13 | $C_{11}H_{14}N_6OS$ | 47.47 47.09 | 5.07 4.98 | 30.20 30.29 | (DMSO—$d_6$) 0.97 (s, 9H) 1.56–1.80 (m, 2H) 2.88–3.16 (m, 2H) | 3196, 2956, 1713, 1575, 1533 |
| 14 | $C_{12}H_{16}N_6OS$ | 49.30 49.11 | 5.52 5.48 | 28.75 28.63 | (DMSO—$d_6$) 0.86 (t, 6H) 1.10–1.90 (m, 7H) 3.03 (m, 2H) | 3154, 2968, 1716, 1578, 1536 |
| 15 | $C_{19}H_{28}N_6OS$ | 58.74 58.58 | 7.26 7.10 | 21.63 21.69 | (CDCl$_3$—TFA) 1.00–1.80 (m, 25H) 3.13 (m, 2H) | 3424, 3100, 2932, 2854, 1713, 1578, 1536 |
| 16 | $C_{15}H_{19}N_5OS$ | 56.76 56.70 | 6.03 6.18 | 22.07 21.93 | (CDCl$_3$) 0.80–1.90 (m, 13H) 2.6–2.8 (m, 2H) 2.79 (s, 3H) | 3034, 2926, 2848, 2776, 1695, 1626, 1584, 1533, 1482 |
| 17 | $C_{13}H_{14}N_6OS$ | 51.64 51.45 | 4.67 4.85 | 27.80 27.23 | (DMSO—$d_6$) 1.0–2.0 (m, 10H) 2.1–2.4 (m, 1H) 6.6–6.7 (m, 2H) | 3160, 2926, 2854, 1710, 1635, 1572, 1533 |
| 18 | $C_{14}H_{18}N_6OS$ | 52.81 52.58 | 5.70 5.81 | 26.40 26.22 | (CDCl$_3$—TFA) 0.93 (d, 3H) 1.05–2.00 (m, 12H) 3.11 (t, 2H) | 2920, 2848, 1713, 1578, 1536 |
| 19 | $C_{15}H_{20}N_6OS$ | 54.20 54.21 | 6.06 6.30 | 25.28 25.19 | (CDCl$_3$—TFA) 1.55 (m, 17H) 3.11 (t, 2H) | 3154, 2914, 2848, 1716, 1575, 1536, 1467, 1449, 1272, 1212, 1149, 1068, 984, 891, 834, 774, 750, 675, 633, 609 |

Syntheses of the starting compounds of formula (VII) used in the above Examples are described in the following Reference Examples 1 to 19. In these Reference Examples, the substituents A and R—X— of the starting materials are identical to those in the compounds of formula (I) of Examples having the corresponding number.

REFERENCE EXAMPLE 1

7-Amino-2-(2-cyclohexylethyl)-6-nitro-5H-[1,3,4]thiadiazolo[3,2-a]pyrimidin-5-one (1) 2-Amino-5-(2-cyclohexylethyl)-[1,3,4]thiadiazole (9.50 g) and 21.8 g of 2,4,6-trichlorophenyl malonate were stirred in 70 ml of xylene at a bath temperature of from 140° to 150° C. for 2 hours. After cooling, the precipitate formed was collected by filtration and washed successively with ethanol and diethyl ether to obtain 10.3 g of 2-(2-cyclohexylethyl)-7-hydroxy-5H-

[1,3,4]thiadiazolo[3,2-a]pyrimidin-5-one as a colorless plate-like crystal.
 Melting point: 215°–219° C.
 Elemental Analysis for $C_{13}H_{17}N_3O_2S$:

| | | | |
|---|---|---|---|
| Calcd. (%): | C: 55.89; | H: 6.13; | N: 15.04 |
| Found (%): | C: 56.04; | H: 6.17; | N: 15.22 |

(2) In 125 ml of acetic acid was suspended 9.77 g of 2-(2-cyclohexylethyl)-7-hydroxy-5H-[1,3,4]thiadiazolo[3,2-a]pyrimidin-5-one, and 3.5 ml of fuming nitric acid was added thereto dropwise while stirring under ice-cooling. The stirring was continued at room temperature for an additional 2.5 hours, and the precipitate formed was collected by filtration and washed successively with water, isopropanol, and diethyl ether to obtain 10.3 g of 2-(2-cyclohexylethyl)-7-hydroxy-6-nitro-5H-[1,3,4]thiadiazolo[3,2-a]pyrimidin-5-one as a pale yellow crystal.
 Melting point: 170°–171° C.
 Elemental Analysis for $C_{13}H_{16}N_4O_4S$:

| | | | |
|---|---|---|---|
| Calcd. (%): | C: 48.14; | H: 4.97; | N: 17.27 |
| Found (%): | C: 47.87; | H: 4.69; | N: 17.41 |

(3) In 30 ml of phosphorous oxychloride was suspended 10.2 g of 2-(2-cyclohexylethyl)-7-hydroxy-6-nitro-5H-[1,3,4]thiadiazolo[3,2-a]pyrimidin-5-one, and 4 ml of tripropylamine was added dropwise to the suspension at room temperature while stirring. The stirring was continued at 80° to 85° C. for an additional 3 hours. After cooling, the reaction mixture was poured into ice-water, and the precipitate formed was collected by filtration and washed with water to obtain 10.4 g of 7-chloro-2-(2-cyclohexylethyl)-6-nitro-5H-[1,3,4]thiadiazolo[3,2-a]pyrimidin-5-one as a crystalline powder.
 Melting point: 136°–137° C.
 Elemental Analysis for $C_{13}H_{15}ClN_4O_3S\cdot\frac{1}{4}H_2O$:

| | | | |
|---|---|---|---|
| Calcd. (%): | C: 44.96; | H: 4.50; | N: 16.13 |
| Found (%): | C: 44.92; | H: 4.38; | N: 16.24 |

(4) In 100 ml of ethanol was suspended 9.59 g of 7-chloro-2-(2-cyclohexylethyl)-6-nitro-5H-[1,3,4]thiadiazolo[3,2-a]pyrimidin-5-one, and 7 ml of concentrated aqueous ammonia was added thereto at room temperature while stirring. The stirring was continued for 5.5 hours. The precipitate formed was collected by filtration and washed successively with ethanol and diethyl ether to obtain 7.05 g of 7-amino-2-(2-cyclohexylethyl)-6-nitro-5H-[1,3,4]thiadiazolo[3,2-a]pyrimidin-5-one as a pale yellow crystal.
 Melting Point: 249°–251° C.
 Elemental Analysis for $C_{13}H_{17}N_5O_3S$:

| | | | |
|---|---|---|---|
| Calcd. (%): | C: 48.28; | H: 5.30; | N: 21.66 |
| Found (%): | C: 48.31; | H: 5.32; | N: 21.66 |

REFERENCE EXAMPLES 2 TO 19

In the same manner as described in Reference Example 1, each of the following compounds represented by formula (VII) of Reference Examples 2 to 19 was prepared.

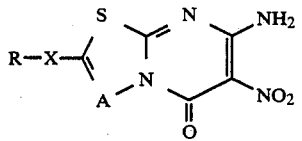

| Compound of Reference Example | Melting Point (°C.) |
|---|---|
| 2 | 238–239 |
| 3 | 225–227 |
| 4 | 274–280 |
| 5 | 238–242 |
| 6 | 250–253 |
| 7 | 238–240 |
| 8 | 241–245 |
| 9 | 252–255 |
| 10 | 200–201 |
| 11 | 200–201 |
| 12 | 175–182 |
| 13 | 264–268 |
| 14 | 243–246 |
| 15 | ~266 (decomp.) |
| 16 | 209–210 |
| 17 | 275–277 (decomp.) |
| 18 | 140–141 |
| 19 | 260–267 |

Syntheses of novel compounds in the starting compounds of formula (III) are described in the following Reference Examples 20 to 35.

REFERENCE EXAMPLE 20

5-(2-Cyclohexylethyl)-1,3,4-thiadiazol-2-amine

3-Cyclohexylpropionitrile (181 g) and 120 g of thiosemicarbazide were dissolved in 40 ml of trifluoroacetic acid, followed by stirring at a bath temperature of 70° to 80° C. for 4 hours. The reaction mixture was poured into ice-water, and 500 ml of concentrated aqueous ammonia was added thereto, followed by stirring at room temperature for 1.5 hours. The resulting precipitate was collected by filtration and washed with successive, small amounts of ethanol and diethyl ether to obtain 197 g of the titled compound.
 Melting point: 253°–255° C.

REFERENCE EXAMPLES 21 TO 35

In the same manner as described in Reference Example 20, each of the following compounds of formula (III) was prepared.

| Reference Example No. | A | R—X— | Melting Point (°C.) |
|---|---|---|---|
| 21 | N | $(CH_3)_3C(CH_2)_2-$ | 240–242 |
| 22 | N | $(CH_3CH_2)_2CH(CH_2)_2-$ | 202–203 |
| 23 | N | cyclopentyl-$(CH_2)_3-$ | 210–212 |
| 24 | N | cyclohexyl-$CH_2-$ | 250–267 |

-continued

| Reference Example No. | A | R—X— | Melting Point (°C.) |
|---|---|---|---|
| 25 | N | 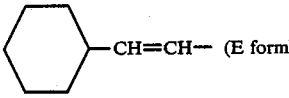 —CH=CH— (E form) | 247–249 (decomp.) |
| 26 | N | 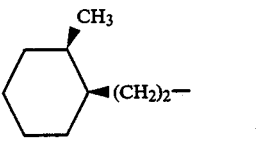 | 234–238 |
| 27 | N | 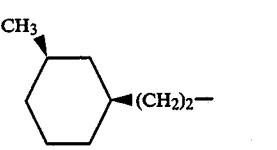 | 238–240 |
| 28 | N | 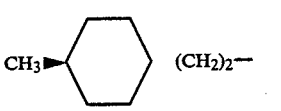 | 269–271 |
| 29 | N | 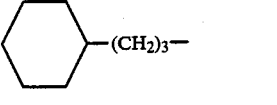 | 227–228 |
| 30 | N | 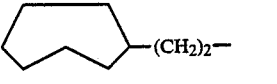 | 250–266 |
| 31 | N | 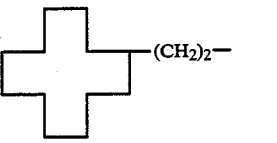 | ~226 (unclear) |
| 32 | N | 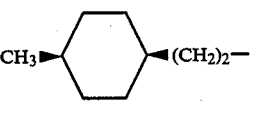 | 210–215 |
| 33 | N | 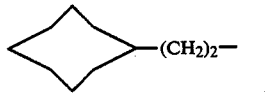 | 248–250 |

REFERENCE EXAMPLE 34

5-(2-Cyclohexylethyl)-2-thiazolamine (1) In 300 ml of dichloromethane was dissolved 100 ml of dioxane, and 46 ml of bromine was added dropwise to the solution. In 200 ml of dichloromethane was dissolved 180 g of 4-cyclohexylbutylaldehyde, and the solution was cooled to $-5°$ C. To the resulting solution was added dropwise the above prepared bromine solution while keeping at $-5°$ to $-2°$ C. After stirring for 30 minutes, an aqueous solution of sodium nitrite was added thereto to decompose excess bromine. After neutralization with a sodium hydroxide aqueous solution, the dichloromethane layer was washed with water and dried. The solvent was removed by distillation to obtain 2-bromo-4-cyclohexylbutylaldehyde as a pale yellow oily substance.

(2) The 2-bromo-4-cyclohexylbutylaldehyde as prepared in (1) above and 76 g of thiourea were dissolved in 700 ml of ethanol, followed by refluxing for 4.5 hours. The reaction mixture was rendered alkaline by addition of a sodium hydroxide aqueous solution, and the ethanol was removed by distillation. The residue was cooled, and the resulting solid was collected by filtration, washed with water, dried, and washed with petroleum ether to obtain 120 g of the titled compound.

Melting point: 98°–99° C.

REFERENCE EXAMPLE 35

5-(2-Cyclopentylethyl)-2-thiazolamine

The titled compound was prepared in the same manner as described in Reference Example 34 from 4-cyclopentylbutylaldehyde.

Melting point: 77°–78° C.

REFERENCE EXAMPLE 36

5-(2-Cyclohexylethyl)-4-methyl-2-thiazolamine

A mixture of 22.2 g of 5-cyclohexyl-2-pentanone, 20.10 g of thiourea, and 33.48 g of iodine was stirred for 23 hours at a bath temperature of from 100° to 120° C. To the mixture was added 150 ml of water, followed by refluxing for 30 minutes. After cooling, an aqueous sodium hydroxide solution was added to neutralize. The mixture was extracted with ethyl acetate, and the extract was washed with water and dried. The solvent was removed by distillation, and the residue was purified by silica gel column chromatography. Recrystallization from aqueous methanol yielded 10.9 g of the titled compound.

Melting point: 98°–100° C.

TEST EXAMPLE 1

LTD$_4$ Antagonistic Activity

The excellent LTD$_4$ antagonistic activity of the compounds according to the present invention was proved by an in vitro inhibitory activity on LTD$_4$-induced ileal contraction in guinea pigs.

Male guinea pigs weighing 300 to 600 g were killed by a sharp blow to the head. The ileum was removed and cut into segments of approximately 2 cm. Each segment was placed in an organ bath containing 5 ml of a Tyrode solution (30°±1° C.) having been aerated with a mixed gas comprising 95% O$_2$ and 5% CO$_2$. Ileal contraction under a load of 0.6 g was measured by the use of an isotonic transducer.

After confirming that a stable contraction reaction took place, 3.0 ng/ml of LTD$_4$ was added to the bath to induce contraction in the presence or absence of test compound. The time for the pretreatment with the test compound was 1 minute, and the degree of contraction induced by LTD$_4$ in the presence of test compound was compared with that in the absence of test compound to obtain a percent inhibition. A concentration for 50% inhibition (IC$_{50}$) was calculated from the resulting percent inhibition.

For comparison, 6-(2-phenylethyl)-[1,3,4]thiadiazolo[3,2-a][1,2,3]triazolo[4,5-d]pyrimidin-9-(1H)-one (the compound of U.S. Pat. No. 4,652,646) was used as a comparative compound. A potency ratio of IC$_{50}$ value of the compound according to the present invention to the IC$_{50}$ value of the comparative compound was calculated, and the results obtained are shown in Table 1 below.

TABLE 1

| Compound of Example | Potency Ratio |
|---|---|
| 1 | 14.8 |
| 2 | 8.2 |
| 3 | 4.4 |
| 5 | 6.9 |
| 6 | 9.5 |
| 7 | 13.4 |
| 9 | 21.4 |
| 10 | 37.0 |
| 11 | 125.4 |
| 16 | 42.7 |
| 17 | 12.3 |
| 18 | 9.0 |
| 19 | 7.2 |

As is apparent from the Table, the compounds according to the present invention exhibit superior $LTD_4$ antagonistic activities to the comparative compound.

TEST EXAMPLE 2

PCA Test (1) Preparation of Antiserum:

Each of Sprague-Dawley female rats weighing 170 to 250 g (CRJ-CD(SD), Charles River Japan Inc.) was intramuscularly administered with 5 mg/kg-body weight of egg albumin dissolved in saline, and then 1 ml of a suspension of *Bordetella pertussis* vaccine ($2 \times 10^{10}$ organism) in saline was administered intraperitoneally to the rat. On day 10, 3,000 larvae animal of *Nippostrongylus brasiliensis* were subcutaneously administered to the rats. On day 24, blood was drawn from the rats to obtain an antiserum. The PCA titer of this serum was found to be 1:128 to 256 when measured with the 48 hours PCA in rats.

(2) PCA Test:

The antiserum was diluted with saline so as to provide a blue spot having a diameter of about 10 mm in the following control group.

Male sprague-Dawley rats weighing about 180 g (5 rats per group) were sensitized by injecting 0.05 ml of the diluted antiserum into the shaved dorsal skin. Forty-eight hours later, 1 ml of saline containing 0.5% Evans blue and 5 mg of egg albumin was administered to each of the rats via a tail vein. After 30 minutes, the rats were sacrificed by decapitation. The dorsal skin was removed, and the amount of the dye in the blue spot area was measured in accordance with the method of Katayama et al., Microbiol. Immunol., Vol. 22, 89–101 (1978).

Ten milligrams of the test compound was suspended in 5 ml of a 0.5% CMC aqueous solution, and the suspension was orally administered to each of the rats in an amount of 10 mg/kg 30 minutes before the antigen challenge. On the other hand, a control group received only a 0.5% CMC solution.

The inhibitory activity on the PCA reaction in the treated group was calculated by the following equation:

$$\text{Inhibition (\%)} = \frac{V - W}{V} \times 100$$

wherein V represents a mean value of the dye amount in the blue spot area in the control group; and W represents a mean value of the dye amount in the blue spot area in the treated group.

The inhibitory activities of the compounds of the present invention are shown in Table 2 below.

TABLE 2

| Compound of Example | Inhibition (%) |
|---|---|
| 1 | 81 |
| 2 | 62 |
| 3 | 91 |
| 4 | 77 |
| 8 | 88 |
| 9 | 88 |

The results of Table 2 apparently demonstrate the excellent PCA inhibitory activity of the compounds according to the present invention.

TEST EXAMPLE 3

Acute Toxicity Test

The acute toxicity ($LD_{50}$) of typical compounds of the present invention is shown in Table 3 below.

TABLE 3

| Compound of Example | $LD_{50}$ (g/kg p.o. in mice) |
|---|---|
| 1 | >4 |
| 2 | 2–4 |
| 3 | >4 |
| 5 | >4 |
| 9 | >4 |

While the invention has been described in detail and with reference to specific embodiments thereof, it will be apparent to one skilled in the art that various changes and modifications can be made therein without departing from the spirit and scope thereof.

What is claimed is:

1. A compound represented by formula (I)

$$R-X-\underset{A-N}{\overset{S}{\underset{\|}{\bigg\langle}}}\overset{N}{\underset{O}{\bigg\rangle}}\overset{N-N}{\underset{H}{\bigg\rangle}} \quad (I)$$

where A represents $$=C- \atop | \atop A'$$

or $=N-$; A' represents a hydrogen atom, an alkyl group or a halogen-substituted alkyl group having 1 to 6 carbon atoms; R represents a cycloalkyl group having 4 to 14 carbon atoms which may be substituted with one or more alkyl groups, having 1 to 6 carbon atoms; and X represents a single bond, or an alkylene group having 1 to 10 carbon atoms or an alkenylene group having 2 to 10 carbon atoms, each of which may be substituted with one or more substituents selected from the group consisting of an alkoxy group having 1 to 6 carbon atoms and a halogen atom, and physiologically acceptable salts thereof.

2. A compound or a salt thereof according to claim 1, wherein X represents an alkylene group having 1 to 10 carbon atoms or an alkenylene group having 2 to 10 carbon atoms.

3. A compound or a salt thereof according to claim 1, wherein X represents an ethylene group, a propylene group or a vinylene group; R represents a cycloalkyl group having from 5 to 7 carbon atoms which may be substituted with an alkyl group; and A represents CH or N.

4. 6-(2-Cyclohexylethyl)-[1,3,4]thiadiazolo-[3,2-a][1,2,3]triazolo[4,5-d]pyrimidin-9-(1H)-one or a salt thereof according to claim 1.

5. 6-(2-Cycloheptylethyl)-[1,3,4]thiadiazolo-[3,2-a][1,2,3]triazolo[4,5-d]pyrimidin-9-(1H)-one or a salt thereof according to claim 1.

6. 6-(2-Cyclopentylethyl)-[1,3,4]thiadiazolo-[3,2-a][1,2,3]triazolo[4,5-d]pyrimidin-9-(1H)-one or a salt thereof according to claim 1.

7. 6-(2-Cyclohexylethyl)-thiazolo[3,2-a]-[1,2,3]triazolo[4,5-d]pyrimidin-9-(1H)-one or a salt thereof according to claim 1.

8. 6-(2-Cyclopentylethyl)-thiazolo[3,2-a]-[1,2,3]triazolo[4,5-d]pyrimidin-9-(1H)-one or a salt thereof according to claim 1.

9. 6-(3-Cyclopentylpropyl)-[1,3,4]thiadiazolo-[3,2-a][1,2,3]triazolo[4,5-d]pyrimidin-9-(1H)-one or a salt thereof according to claim 1.

10. 6-(3-Cyclohexylpropyl)-[1,3,4]thiadiazolo-[3,2-a][1,2,3]triazolo[4,5-d]pyrimidin-9-(1H)-one or a salt thereof according to claim 1.

11. 6-[2-(cis-2-Methylcyclohexyl)ethyl]-[1,3,4]thiadiazolo[3,2-a][1,2,3]triazolo[4,5-d]pyrimidin-9-(1H)-one or a salt thereof according to claim 1.

12. 6-[2-(cis-3-Methylcyclohexyl)ethyl]-[1,3,4]thiadiazolo[3,2-a][1,2,3]triazolo[4,5-d]pyrimidin-9-(1H)-one or a salt thereof according to claim 1.

13. 6-[2-(trans-4-Methylcyclohexyl)ethyl]-[1,3,4]thiadiazolo[3,2-a][1,2,3]triazolo[4,5-d]pyrimidin-9-(1H)-one or a salt thereof according to claim 1.

14. 6-[2-(cis-4-Methylcyclohexyl)ethyl]-[1,3,4]thiadiazolo[3,2-a][1,2,3]triazolo[4,5-d]pyrimidin-9-(1H)-one or a salt thereof according to claim 1.

15. 6-[(E)-2-cyclohexylethenyl][1,3,4]thiadiazolo[3,2-a][1,2,3]triazolo[4,5-d]pyrimidin-9-(1H)-one or a salt thereof according to claim 1.

* * * * *